(12) United States Patent
Johansson et al.

(10) Patent No.: US 7,309,496 B2
(45) Date of Patent: Dec. 18, 2007

(54) COMPOSITION

(75) Inventors: Marie Johansson, Watchung, NJ (US); Josh Ghaim, Franklin Park, NJ (US); Nadia Soliman, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 384 days.

(21) Appl. No.: 10/612,549

(22) Filed: Jul. 2, 2003

(65) Prior Publication Data

US 2005/0002973 A1 Jan. 6, 2005

(51) Int. Cl.
*A61K 8/00* (2006.01)
*A61K 8/02* (2006.01)

(52) U.S. Cl. ...................... 424/401; 510/130
(58) Field of Classification Search ............... 424/401; 510/152

See application file for complete search history.

(56) References Cited

U.S. PATENT DOCUMENTS

| | | | |
|---|---|---|---|
| 2,438,091 A | 3/1948 | Lynch | |
| 3,277,013 A | 10/1966 | Gianladis | |
| 3,645,904 A | 2/1972 | Beach | |
| 4,035,514 A | 7/1977 | Davis | |
| 4,155,870 A | 5/1979 | Jorgensen | |
| 4,673,526 A | 6/1987 | Zabotto et al. | |
| 4,784,788 A | 11/1988 | Lancz | |
| 5,246,613 A | 9/1993 | Gilbert et al. | |
| 5,266,321 A | 11/1993 | Shukuzaki et al. | |
| 5,431,913 A | 7/1995 | Phillips | |
| 5,527,488 A | 6/1996 | Groh | |
| 5,679,326 A | 10/1997 | Bara et al. | |
| 5,830,445 A | 11/1998 | Bouillon et al. | |
| 5,888,951 A | 3/1999 | Gagnebien et al. | |
| 5,891,449 A | 4/1999 | Daniel et al. | |
| 6,013,270 A | 1/2000 | Hargraves et al. | |
| 6,103,644 A | 8/2000 | Sheridan | |
| 6,120,759 A | 9/2000 | Bouillon | |
| 6,217,889 B1 | 4/2001 | Lorenzi et al. | |
| 6,290,976 B1 | 9/2001 | Messenger | |
| 6,524,594 B1 | 2/2003 | Santora et al. | |
| 2003/0133900 A1 | 7/2003 | McLaughlin | |
| 2003/0211062 A1 | 11/2003 | Laden et al. | |
| 2004/0198620 A1 | 10/2004 | Johansson et al. | |
| 2005/0158351 A1 | 7/2005 | Soliman et al. | |

FOREIGN PATENT DOCUMENTS

CN 1088776 7/1994
WO WO 01/85103 A1 5/2001

OTHER PUBLICATIONS

Flick, E., Cosmetics Additives: An Industrial Guide, 1991, Noyes Publication, p. 215.*
Prosecution History from U.S. Appl. No. 10/406,123.

* cited by examiner

*Primary Examiner*—Sreeni Padmanabhan
*Assistant Examiner*—Gina Yu
(74) *Attorney, Agent, or Firm*—Michael F. Morgan

(57) ABSTRACT

1. A composition which is at least substantially anhydrous and comprises
   a. At least one water immiscible emollient oil in sufficient quantity to provide emollience to skin,
   b. At least one emulsifying agent capable of forming an emulsion, in situ, on the skin with the above oil when water is added to the said composition, the said emulsifier in such quantities that the oil is substantially removed from the skin,
   c. A physical stabilization of the composition enhancing amount of a component selected from the group consisting of
   1) At lease one wax,
   2) At lease one oil gelling agent that is both water and oil insoluble, and
   3) A mixture of 1 and 2.

2 Claims, No Drawings

COMPOSITION

BACKGROUND OF THE INVENTION

Aqueous skin cleansing compositions have been used for centuries. Washing the skin with various surface-active preparations several times a day results in the swelling of the horny layers, with water insoluble constituents of dirt being washed off and substances endogenous to the skin being washed out. During this process, naturally occurring skin fats are also removed causing over-drying of the skin, thus making it necessary to replenish the skin with moisturizers such as creams and lotion based on oil-in-water and water-in-oil emulsions.

The most common way of replenishing the skin with moisturizers is to use mild cleansers for showering and then apply an aqueous based emulsion, for example, an oil-in-water emulsion such as creams and lotions after showering. These steps are time consuming and not the most effective methods of moisturizing the skin. The most effective way to moisturize the skin seems to be to lock-in moisture while wet. Prior attempts have been made to overcome the foregoing problems of skin cleansers by the use of emulsion based creams and lotions and by employing anhydrous skin cleansers. Anhydrous skin cleansers, sometimes called waterless cleansers, typically contain high concentrations of water-insoluble solvents, which makes them generally effective at removing oily undesirables from the skin but less effective in removing water soluble undesirables. Further, anhydrous skin cleansers typically are not cosmetically elegant tending to have a heavy, greasy feel making them unappealing to the touch and are not easily removed from the skin. They generally must be wiped off with toweling, leaving the skin feeling greasy or need to be washed off with strong soap, leaving the skin feeling harsh and dry to the user.

Various solutions to these problems have been proposed in the prior art. For example, U.S. Pat. No. 6,524,594 relates to a gelled oil skin cleansing compositions and to uses thereof. These compositions are not only effective, foaming cleansers, but they are alleged to leave a light moisturizing feel to the skin after rinsing. U.S. Pat. No. 4,673,526 proposes an anhydrous three component system designed for skin cleansing having a solid particulate matter of various polymers to remove oily particles while being essentially multiphase. The publication WO 01/85103 discloses a substantially anhydrous four component system comprising a) at least one water-immiscible cosmetic emollient oil, the cosmetic emollient oil comprising a major portion of the formulation; b) at least one oil-gelling agent that is both water-insoluble and oil-insoluble; c) at least one emulsifying agent capable of forming an emulsion, in situ, on the skin when a small amount of water is added gradually to the substantially anhydrous formulation during use; and d) a substantially crystalline water-soluble, abrasive material that is substantially insoluble in the substantially anhydrous vehicle of the formulation.

However, each one of them is not totally satisfactory in at least one parameter. A composition within U.S. Pat. No. 6,524,594 describes a foaming system with high oil content. While these forms are a significant improvement over traditional cleansers, the fact that they generate a significant amount of foam would indicate they will remove a significant amount of the moisturizing oils. The U.S. Pat. No. 4,673,526 patent composition is limited to cleansing by removal of oil substances on the skin without the addition of fat bodies to the skin. The WO 01/85103 composition is thought to be removed from the skin with a relatively small amount of water, preferably up to 2 parts of the actual oily composition on the skin. These, and other disadvantages can be overcome by the discovery and use of a new at least substantially anhydrous skin cleansing composition.

The present invention of at least substantially anhydrous rinse-off skin conditioners provide effective skin moisturizing and conditioning in a cosmetically pleasing aesthetic vehicle, thus leaving the skin exceptionally soft, smooth and moisturized after use. The composition has at least enhanced phase stability, is easily applied to the skin while wet in the shower, and can be effectively removed from the skin with varying amounts of water, leaving the skin with perceivable and desirable sensory attribute during and after use. This composition can eliminate the need for use of a cream or a lotion after showering.

SUMMARY OF THE INVENTION

In accordance with the invention, there is a conditioner composition which is at least substantially anhydrous and comprises:
  a) at least one water insoluble emollient oil in sufficient quantity to provide emolliency to the skin,
  b) at least one emulsifying agent capable of forming an emulsion in situ on the skin with the above oil when water is added to the said composition,
  c) a physical stabilization of the composition enhancing amount of a component selected from the group consisting of:
    1. at least one wax
    2. at least one oil gelling agent that is both water and oil insoluble, and
    3. a mixture of 1 and 2.

A further aspect of the invention is the application of this composition to the skin, working the composition into the skin while wet, adding water to the composition on the skin with optional continual working into the skin, and then removing from the skin as a solution or an aqueous emulsion.

DETAILED DESCRIPTION OF THE INVENTION

At least one water immiscible emollient oil component is present in the composition. Illustrative examples of the oil(s) include:
  a) Mineral oils: paraffin oil, petroleum jelly oil
  b) Animal oils: purcellin oil, perhydrosqualene, fish oils and lanolin oil
  c) Vegetable oils: sweet almond oil, palm oil, calophyllum oil, avocado oil, olive oil, castor oil, cereal germ oil such as oil of wheat germ, canola oil, sunflower oil, soybean oil and jojoba oil.
  d) Silicone oils and waxes: dimethylpolysiloxane, cyclomethicone, stearyl dimethicone
  e) Esters: butyl myristate, isopropyl myristate, cetyl myristate, isopropyl palmitate, butylstearate, hexadecyl, stearate, isopropyl stearate, octyl stearate, isoceryl stearate, decyl oleate, hexyl laurate di-caprylate of proplyene glycol, di-isopropyl adipate
  f) The organic alcohols: oleic alcohol, linoleic alcohol, linolenic alcohol, isostearyl alcohol, octyl dodecanol
  g) The esters derived from lanolic acid: isopropyl lanolate, isocetyl lanolate h) Free fatty acid including linoleic, myristic, palmitic, stearic and the like In addition to the classes of the compounds mentioned above, one can also utilize as additional illustrative oils the acetyl glycerides, the octanoates and decanoates of alcohols and polyalcohols such as those of glycol and glycerol, the ricinoleates of alcohols and polyalcohols such as that of cetyl.

The oil or oils can be in the composition at a minimum of about 15, 20, 25, or 30 wt % of the composition. The maximum amount of oil can be up to about 85, 75, 65, or about 60 wt % of the composition.

The emulsifier, component b, is also an important portion of the composition. The ability to emulsify the oil, component a, when water is added, is a significant effect of the composition. This provides a clean surface to the skin after water is added but still allows the skin to benefit from the emolliency of the oil. To facilitate the forming of an emulsion upon the first addition of water to the composition in contact with the skin more than one emulsifier can be employed. It is preferred to use a mixture of at least two emulsifiers, one having a relatively low HLB value preferable of not more than 8, more preferably in the range of about 3 to about 7, and one having a relatively high HLB of preferably at least 8, more preferably in the range of about 10 to about 19. "HLB" refers to the well known calculated Hydrophile-Lipophile-Balance value assigned to emulsifiers, most commonly nonionic emulsifiers, relating to the water solubility of the emulsifier. An explanation of the HLB system is given in "The HLB System, A Time Saving Guide to Emulsifier Selection" by ICI Americas, Inc., Wilmington, Del., 19897, 1984.

The anhydrous skin compositions of the present invention readily form an emulsion when the anhydrous skin composition is contacted with water. Thus, this invention beneficially retains the skin moisturization and conditioning efficacy without an unwanted oily residue but leaving the skin feeling smooth and moisturized.

Exemplary emulsifying agents include, without being limited thereto, ethoxylated carboxylic acids, ethoxylated glycerides, glycol esters and derivatives thereof, monoglycerides, polyglyceryl esters, polyhydric alcohol esters and esters, sorbitan/sorbitol esters, triesters of phosphoric acid, ethoxylated-fatty alcohols, propoxylated polyoxyethylene (POE) esters and the like and mixtures thereof. Particularly preferred are glyceryl stearate, PEG-100 stearate, sorbitan stearate, PEG-40 stearate, steareth-2, steareth-20, steareth-100, polysorbate-20, laureth-12, laureth-23, polysorbate 80, sucrose distearate, glyceryl oleate, and the like as well as mixtures thereof.

Generally, at least about 1 wt % of the composition is emulsifier(s), or at least about 2 wt %. Usually no more than about 15 wt % of an emulsifier(s), based upon weight of the composition, is necessary, though no more than about 10 wt % can also be employed.

Component c is the material that provides enhanced phase stabilization to the composition. Phase integrity of the overall composition is substantially improved. It is preferred that both c 1 and c 2 are present. When c1 is absent, the overall moisturization and conditioning efficacy of the product is reduced and the composition has more of a tendency to disperse into separate phases at high temperature, the lighter oil phase rising to the top with the heavier materials sinking to the bottom. This provides an unpleasing appearance to the composition, particularly when it is in a container wherein the composition is "scooped" therefrom as well as presenting a serious potential issue of using a composition richer in one component and/or poorer in one component each time the composition is employed. When c2 is absent the stabilization is not as significantly enhanced. When both c1 and c2 are employed together the combination brings about increased sensory attributes such as moisturization and conditioning as well as the enhanced phase stabilization as exemplified by the visually homogeneous phase of the composition or at least essentially visually homogeneous phase. With a physically stable phase present, the delivery (storage) vehicle possibilities are expanded substantially. For example, the composition can be loaded into a container such as a tube capable of deformation wherein a uniform or at least substantially uniform composition can be delivered to the skin upon pressure deformation of the container's exterior.

Illustrative examples of waxes include:
1. The mineral waxes: microcrystalline waxes, paraffin, petroleum jelly,
2. The fossil waxes: ozokerite, montan wax,
3. Animal waxes. beeswax, spermaceti, lanolin wax, lanolin derivatives such as lanolin alcohols, hydrogenated lanolin, hydroxylated lanolin, acetylated lanolin, fatty acids of lanolin, acetylated lanolin, fatty acids of lanolin, acetylated lanolin alcohol,
4. Vegetable waxes, candelila wax, carnauba wax, sumac wax, cocoa butter wax, and shea butter,
5. Hydrogenated waxes which are solid at 25° C.: hydrogenated castor oil, hydrogenated palm oil, hydrogenated tallow, hydrogenated cocoa oil, hydrogenated soy oil,
6. Synthetic oils: polyethylene, copolymerized polyethylene waxes,
7. The fatty esters which are solid at 25° C.: monomyristate of propylene glycol, myristyl myristate,
8. Silicone oils: methyloctadecane-oxypolysiloxane and poly (dimethylsiloxy) stearoxysiloxane, dimethicone, cyclomethicone.

Among the waxes, the following compounds can also be utilized: Cetyl alcohol, stearyl alcohol, the mono-, di- and tri glycerides which are solid at 25° C., stearic monoethenolamide, colophane and its derivatives such as abietates of glycol and glycerol, the sucroglycerides. In general, a wax is a long chain hydrocarboanaecous material which is at least substantially solid at 25° C. and is preferably solid.

The quantity of wax employed in the composition is that amount which enhances phase stabilization. An additional advantage is increased moisturization and conditioning of the skin. Generally, at least about 0.5, 1. 1.5, or 2 wt % of the composition can be employed, desirably at least about 2 or 3 wt %. Usually no more than about 7, 10 or 15 wt % of the composition is wax. Mixtures of waxes can be employed.

Component c2 is the oil-gelling agent. Examples of oil-gelling agents that can be used include, without being limited thereto, silicas, clays and organically modified clays and mixtures thereof. Exemplary oil-gelling silicas preferably include, without being limited thereto, finely divided silicas, magnesium aluminum silicate and the like. Suitable silicas are commercially sold under the trade names Aerosil (Degussa) and Cab-O-Sil (Cabot Corp.). Exemplary oil-gelling clays and organically modified clays preferably include, without being limited thereto, bentonites, hectorites, organophilic clays such as Stearalkonium hectorite, Quaternium-18 hectorite, Quaternium-18 bentonite and the like.

The quantity of oil gelling agent is that which enhances phase stabilization. Generally, at least about 0.5, 1. 1.5, or 2 wt % of the composition can be employed, desirably at least about 2 or 3 wt %. Usually no more than about 7, 10 or 15 wt % of the composition is wax. Mixtures of waxes can be employed.

With respect to various terms employed in the specification and claims "substantially anhydrous" means less than about 5 wt % water in the composition, preferably less than about 3 wt % water, more preferably less than about 1.5 wt % water and most preferably 0 to about 1 wt % water. In measuring the water amount, any water of crystallization is not counted in "substantially anhydrous".

The viscosity of the composition is generally that of a thick liquid or gel but can reach a paste like consistency. Generally, the viscosity is a minimum of about 5,000 10,000 or 15,000 preferably about 20,000 to a maximum of about 12,000,000, 2,000,000 or even about 600,000 cps.

Viscosity is measured by standard techniques such as the use of a Brookfield Viscometer. Those skilled in the art will use the appropriate spindle and speed combination to cover the range of viscosity to be measured. For less viscous samples, Brookfield spindle #5, at 20 rpm and 20° C. is suitable. At high viscosities, a helipath attachment is used with, for example, spindle T-E at 2.5 rpm and 20° C. For example, a preferred range of viscosity of about 500,000 to 1,200,000 cps is measured with a Brookfield viscometer using a helipath attachment with a T-E spindle at 2.5 rpm and about 20° C.

The anhydrous skin compositions of this invention can be prepared by heating together the emollient water-immiscible oil ingredients and emulsifier ingredients to a temperature of about 70° C. with sufficient mixing agitation to dissolve the emulsifier in the oil to provide a substantially anhydrous oil-emulsifier phase. The wax and/or the oil gelling agent is then dispersed with mixing agitation in the anhydrous oil-emulsifier phase until a substantially non-runny, thickened phase begins to form, cooling the admixture, if necessary. Fragrance and other benefit ingredients can be added during the cooling phase, if desired. Those skilled in the art will understand that the order of incorporation of ingredients and temperatures employed may vary with the type of ingredient and the manner of dissolution recommended by the supplier of the material.

A preferred embodiment for using substantially anhydrous skin compositions formulated according to the invention comprises the following steps:

a) Applying the anhydrous skin conditioner to wet skin right after cleansing and/or wetting, preferably by manually rubbing the applied amount over the skin to thoroughly coat the skin. The rubbing action preferably is a gentle rubbing or massaging for a period of at least about 5 second, preferably about 5 to about 30 seconds to spread all over the skin.

b) Contacting the skin conditioner coated skin with an amount of water sufficient to moisten the coated skin, further continuously rubbing and massaging the so-moistened skin and thus resulting in the formation of an emulsion in situ on the skin as a change in the appearance of the substantially transparent or translucent coating to a substantially turbid (i.e., milky to opaque) liquid emulsion.

c) Removing the resultant emulsion from the skin, preferably by rinsing it off with additional water. The intermediate step b need not be followed. Effective skin emolliency and removal of the composition can both be accomplished by adding water of small, medium or large quantities. The skin can then be dried.

It is recognized that in step "c" the emulsion can also be wiped off first and the wiped skin can then be rinsed. Preferably, the novel skin compositions are readily and conveniently removable from the skin by rinsing with water, thereby eliminating the need for tissues or towels and avoiding disposal or laundry problems attendant with the use thereof.

Anhydrous skin formulations prepared with the component and ranges disclosed possess a surprising combination of beneficial effects when used on skin. The anhydrous skin compositions can moisturize and condition the skin leaving it smooth and supple for hours, thus eliminating the need for the use of creams or lotions after the shower.

The following examples further illustrate the anhydrous skin compositions of this invention with specific embodiments, ingredients and methods but are not intended to be limiting.

Below is a preferred example together with various preferences; all numbers are approximate and in wt %:

EXAMPLE 1

20-95% oil, for example a vegetable oil like canola oil, preferably 40-90, more preferably 60-85

0-15% stearic acid, preferably 2-15%, more preferably 2-12

0.25-6% of glycerol stearate preferably 0.5-5%, more preferably 0.75-4%

0.25-6% PEG-100 stearate preferably 0.5-5%, more preferably 0.75-4%

0.05-8% glyceryl oleate preferably 0.1-5%, more preferably 0.3-2%

0.05-5% sucrose distearate preferably 0.1-3%, more preferably 0.2-2%

0-5% shea butter preferably 0.1-4%, more preferably 0.2-3%

0.1-5% cetyl alcohol preferably 0.3-3%, more preferably 0.5-2%

0.5-5% stearyl alcohol preferably 0.3-3%, more preferably 0.5-2%

0.5-8% beeswax preferably 0.75-7%, more preferably 1-5%

0.05-5% carnuba wax preferably 0.1-3%, more preferably 0.2-2%

0.05-8% silica preferably 0.5-6%, more preferably 1-5%

0.05-5% polysorbate-80 preferably 0.1-3%, more preferably 0.2-2%

0-10% colloidal oatmeal preferably 0.5-8%, more preferably 1-5%, 0-5% silicone oil 0-5% minor/beneficial ingredients (fragrance, dyes, vitamins, etc.)

EXAMPLE 2

| Components | Wt % |
| --- | --- |
| Canola oil | 40.05 |
| Mineral Oil | 40.05 |
| Carnuba Wax | 0.75 |
| PEG-100-Stearate | 2.25 |
| Glycerol Stearate | 2.25 |
| Sucrose Distearate | 0.75 |
| Shea butter | 2.00 |
| Cetyl alcohol | 1.50 |
| Stearyl alcohol | 1.80 |
| Glyceryl Oleate | 1.00 |
| White beeswax | 4.00 |

-continued

| Components | Wt % |
|---|---|
| Polysorbate 80 | 1.00 |
| Amorphous fumed silica | 1.50 |
| Titanium dioxide | 0.10 |
| Fragrance | 1.00 |
| Totals | 100.00 |

The invention claimed is:

1. A composition comprising:
 a) about 40 to about 90 weight % vegetable oil,
 b) 0 to about 15 weight % stearic acid,
 c) about 0.25 to about 6 weight % glycerol stearate,
 d) about 0.25 to about 6 weight % PEG-100 stearate,
 e) about 0.05 to about 8 weight % glyceryl oleate,
 f) about 0.05 to about 5 weight % sucrose distearate,
 g) 0 to about 5 weight % shea butter,
 h) about 0.1 to about 5 weight % cetyl alcohol,
 i) about 0.5 to about 5 weight % stearyl alcohol,
 j) about 0.5 to about 8 weight % beeswax,
 k) about 0.05 to about 5 weight % carnauba wax,
 l) about 0.05 to about 8 weight % silica,
 m) about 0.05 to about 5 weight % polysorbate-80,
 n) 0 to about 10 weight % colloidal oatmeal, and
 o) 0 to about 5 weight % silicone oil.

2. A composition comprising about 40.05 weight % canola oil, about 40.05 weight % mineral oil, about 0.75 weight % carnauba wax, about 2.25 weight % PEG-100 stearate, about 2.25 weight % glycerol stearate, about 0.75 weight % sucrose distearate, about 2 weight % shea butter, about 1.5 weight % cetyl alcohol, about 1.8 weight % stearyl alcohol, about 1 weight % glyceryl oleate, about 4 weight % white beeswax, about 1 weight % polysorbate 80, about 1.5 weight % amorphous fumed silica, and about 0.1 weight % titanium dioxide.

* * * * *